(12) United States Patent
Harel et al.

(10) Patent No.: US 10,265,510 B2
(45) Date of Patent: Apr. 23, 2019

(54) MEANS AND METHODS FOR TARGETED X-RAY THERAPY

(71) Applicant: CONVERGENT R.N.R LTD, Tirat Carmel (IL)

(72) Inventors: Zeev Harel, Kfar Saba (IL); Zeev Burshtein, Nes-Ziona (IL); Aharon Bar-David, Nesher (IL); Miri Markovich, Haifa (IL)

(73) Assignee: CONVERGENT R.N.R LTD, Tirat Carmel (IL)

( * ) Notice: Subject to any disclaimer, the term of this patent is extended or adjusted under 35 U.S.C. 154(b) by 272 days.

(21) Appl. No.: 15/503,006

(22) PCT Filed: Aug. 12, 2015

(86) PCT No.: PCT/IL2015/050824
§ 371 (c)(1),
(2) Date: Feb. 10, 2017

(87) PCT Pub. No.: WO2016/024279
PCT Pub. Date: Feb. 18, 2016

(65) Prior Publication Data
US 2017/0232245 A1 Aug. 17, 2017

Related U.S. Application Data

(60) Provisional application No. 62/036,624, filed on Aug. 13, 2014.

(51) Int. Cl.
*A61M 37/00* (2006.01)
*A61N 5/10* (2006.01)
(Continued)

(52) U.S. Cl.
CPC .......... *A61M 37/00* (2013.01); *A61K 9/0009* (2013.01); *A61K 41/00* (2013.01);
(Continued)

(58) Field of Classification Search
None
See application file for complete search history.

(56) References Cited

U.S. PATENT DOCUMENTS 5,962,424 A   10/1999  Hallahan et al.
6,159,443 A * 12/2000  Hallahan ............ A61K 41/0038
                                                 424/1.17
(Continued)

FOREIGN PATENT DOCUMENTS

WO    2012/023141 A1    2/2012
WO    2016/024279 A1    2/2016

OTHER PUBLICATIONS

International Search Report for PCT/IL2015/050824, dated Nov. 30, 2015.
(Continued)

*Primary Examiner* — Hoon K Song

(57) ABSTRACT

The present invention provides a method for activating a pro-drug in vivo comprising the steps of: (a) administering a pro-drug to a subject; (b) locating a target site which has been at least partially dosed with the pro-drug at a predetermined concentration; and (d) exposing the target site to X-ray radiation. The step of exposing the target site to X-ray radiation is characterized by providing a converging X-ray of a controllable waist, substantially uniform at the target site, sufficient to convert the pro-drug to an active drug, while the X-ray photon dosage at the target site is higher than the X-ray photon dosage at an adjacent non target site.

20 Claims, 3 Drawing Sheets

(51) Int. Cl.
A61K 41/00 (2006.01)
A61K 9/00 (2006.01)
(52) U.S. Cl.
CPC .......... *A61K 41/0052* (2013.01); *A61N 5/10* (2013.01); *A61M 2037/0007* (2013.01); *A61N 2005/1091* (2013.01); *A61N 2005/1098* (2013.01)

(56) References Cited

U.S. PATENT DOCUMENTS

| | | | | |
|---|---|---|---|---|
| 6,576,257 | B1* | 6/2003 | Yarmut | A61K 41/0028 424/450 |
| 8,808,733 | B2* | 8/2014 | Fologea | A61K 9/127 424/450 |
| 2013/0017266 | A1 | 1/2013 | Ogino et al. | |

OTHER PUBLICATIONS

Written Opinion of the International Search Authority for PCT/IL2015/050824, dated Nov. 30, 2015.
International Preliminary Report on Patentability (Chapter II) for PCT/IL2015/050824, dated Jan. 9, 2017.
Hirata N. et al., "Radiolytic activation of a cytarabine prodrug possessing a 2-oxoalkyl group: one-electron reduction and cytotoxicity characteristics", Organic & Biomolecular Chemistry, Issue 7, Mar. 2009, pp. 651-654.
Townley H.E. et al., "Nanoparticle augmented radiation treatment decreases cancer cell proliferation", Nanomedicine, May 2012, vol. 8, Issue 4, pp. 526-536.
Scaffidi J.P. et al., "Activity of psoralen-functionalized nanoscintillators against cancer cells upon X-ray excitation", ACS Nano, Jun. 2011, vol. 28, Issue 5(6), pp. 4679-4687.
Hainfeld et al., "Gold nanoparticles enhance the radiation therapy of a murine squamous cell carcinoma", Phys. Med. Biol., 2010, vol. 55, pp. 3045-3059.
Shrinidh J. et al., "Rivastigmine-loaded PLGA and PBCA nanoparticles: Preparation, optimization, characterization, in vitro and pharmacodynamic studies", European journal of pharmaceutics and biopharmaceutics: official journal of Arbeitsgemeinschaft fur Pharmazeutische Verfahrenstechnik e.V, Oct. 2010, vol. 76(2), pp. 189-199.
Kreiter J. et al., "Apolipoprotein-mediated Transport of Nanoparticle-bound Drugs Across the Blood-Brain Barrier", Journal of Drug Targeting, 2002, vol. 10 (4), pp. 317-325.
Juillerat-Jeanneret L., "The targeted delivery of cancer drugs across the blood-brain barrier: chemical modifications of drugs or drug-nanoparticles?", Drug Discov Today, Dec. 2008, vol. 13, Issue 23-24, pp. 1099-1106.

* cited by examiner

MEANS AND METHODS FOR TARGETED X-RAY THERAPY

CROSS-REFERENCE TO RELATED APPLICATIONS

This application is a U.S. National Phase filing under 35 U.S.C. 371 of International (PCT) Patent Application No. PCT/IL2015/050824, filed Aug. 12, 2015, which claims priority from U.S. Provisional Patent Application No. 62/036,624, filed Aug. 13, 2014, both of which are incorporated by reference in their entirety.

FIELD OF THE INVENTION

The current invention pertains to a method and device for activating a pro-drug in a specific target site with increased effectiveness and reduced adverse effects by using a converging x-ray beam.

BACKGROUND OF THE INVENTION

Chemotherapy is the treatment of cancer with one or more cytotoxic antineoplastic drugs as part of a standardized regimen. Most chemotherapeutic agents act by killing cells that divide rapidly, one of the main properties of most cancer cells. This means that chemotherapy also harms cells that divide rapidly under normal circumstances: cells in the bone marrow, digestive tract, and hair follicles, which result in the most common side-effects of chemotherapy: decreased production of blood cells, inflammation of the digestive tract lining, and hair loss.

Most of the conventional chemotherapeutic agents have poor pharmacokinetics profiles and are distributed non-specifically in the body leading to systemic toxicity associated with the above mentioned side effects. Therefore, the development of drug delivery systems able to target the tumor site is becoming a real challenge that is currently addressed.

Targeted therapy is one approach for overcoming the non-specificity of the chemotherapeutic agents. In this approach the chemotherapeutic agents block the growth of cancer cells by interfering with specific targeted molecules needed for carcinogenesis and tumor growth, rather than by simply interfering with all rapidly dividing cells. Using nano-carriers is an additional developing tactic for specifically delivering the chemotherapeutic agents to their target. The nano-carriers are able to target the drug to the tumor site and specifically deliver it there, thereby reducing the damage to normal tissues.

In another approach, an inactive form (pro-drug) of a therapeutic agent is systematically introduced and then specifically activated by external high-energy ionizing radiation aimed explicitly to the target site. For example, U.S. Pat. No. 6,159,443 recites a method in which a target tissue is exposed to ionizing radiation before, after, or in parallel to the administration of a delivery vehicle which is platelets or proteins which bind activated platelets, comprising an active agent. The ionizing radiation induces an inflammatory response which causes the delivery vehicle to aggregate in the target tissue and thereby deliver the agent to the target tissue. Another example can be found in U.S. Pat. No. 5,962,424 which discloses a method for specifically targeting L-selectin or E-selectin binding agents by ionizing radiation. It is disclosed in U.S. Pat. No. 5,962,424 that the ionizing radiation induces L-selectin or E-selectin expression on the surface of vasculature endothelial cells.

In the above examples, the ionizing radiation is administered to the treated subject to produce an effect on a tissue that will enable the drug specificity. Furthermore, the ionizing radiation also affects regions preceding and following the target tissue, thus damaging healthy tissue which will cause adverse effects. In addition, if not delivered by a beam having a sufficient dosage specifically at the target site, the ionizing radiation will also activate tissues or molecules surrounding the target area.

There thus remains a long felt need for a method and device that will deliver ionizing radiation for activating a pro-drug in an effective manner that will not cause its activation in tissues preceding or following the target tissue nor in tissues surrounding the target tissue.

SUMMARY

It is one object of the present invention to provide a method for activating a pro-drug in vivo comprising the steps of (a) administering a pro-drug to a subject; (b) locating a target site which has been at least partially dosed with the pro-drug at a predetermined concentration; and (c) exposing the target site to X-ray radiation; wherein the step of exposing the target site to X-ray radiation is characterized by providing a converging X-ray of a controllable waist, substantially uniform at the target site, sufficient to convert the pro-drug to an active drug, whilst the X-ray photon dosage at the target site is higher than the X-ray photon dosage at an adjacent non target site.

It is another object of the present invention to provide the method as defined above, comprising additional steps of exposing the target site to X-ray characterized by photon energy of up to 500 keV, particularly up to 250 keV.

It is another object of the present invention to provide the method as defined in any of the above, comprising additional steps of exposing the target site to X-ray characterized by photon energy in the range of between about 30 keV and about 180 keV.

It is another object of the present invention to provide the method as defined in any of the above, comprising additional steps of providing an in vivo reservoir of pro-drug and exposing the reservoir of pro-drug to X-ray in a predetermined manner to convert a predetermined quantity of the pro-drug to an active drug.

It is another object of the present invention to provide the method as defined in any of the above, comprising additional steps of exposing the target site to an X-ray administering protocol comprising a cell killing mode and a pro-drug-activating mode.

It is another object of the present invention to provide the method as defined in any of the above, comprising additional steps of providing the X-ray administering protocol modes simultaneously, interchangeably or sequentially.

It is another object of the present invention to provide the method as defined in any of the above, comprising an additional step of exposing the target site to X-ray doses in the range of between about 20 Gy to about 80 Gy or to any other dosing protocol.

It is another object of the present invention to provide the method as defined in any of the above, comprising an additional step of exposing the target site to X-ray doses in the range of between about 20 Gy to about 80 Gy, provided in 1.8 to 4 Gy fractions, or in any other dose fractionating protocol.

It is another object of the present invention to provide the method as defined in any of the above, comprising an additional step of exposing the target site to a radiotherapy protocol or to a radiosurgery protocol or to a combination thereof.

It is another object of the present invention to provide the method as defined in any of the above, comprising an additional step of exposing the target site to X-ray radiation after or during or a combination thereof, administering the pro-drug.

It is another object of the present invention to provide the method as defined in any of the above, comprising an additional step of designing the pro-drug so as to be activated after an enzymatic or chemical reaction.

It is another object of the present invention to provide the method as defined in any of the above, comprising an additional step of activating the enzymatic or chemical reaction by exposure to X-ray radiation: wherein the step of exposure to X-ray radiation is characterized by providing a converging X-ray of a controllable waist, substantially uniform at the target site, sufficient to convert the pro-drug to an active drug, whilst the X-ray photon dosage at the target site is higher than the X-ray photon dosage at an adjacent non target site.

It is another object of the present invention to provide the method as defined in any of the above, comprising an additional step of selecting the pro-drug from the group consisting of oligonucleotides, antisense oligonucleotides, lipids, chemical molecule, chemical derivatives, biological molecules or derivatives thereof, precursors, analogs, antibodies, genes, enzymes, amino acids, proteins, metabolites, enantiomers, glycoproteins, lipoproteins, viral vectors, and any combination thereof.

It is another object of the present invention to provide the method as defined in any of the above, comprising an additional step of selecting the pro-drug from the group of types based on bioactivation site, consisting of intracellular site, extracellular site, and a combination thereof.

It is another object of the present invention to provide the method as defined in any of the above, comprising an additional step of selecting the pro-drug from the group of types based on tissue location of bioactivation, consisting of therapeutic target tissues or cells, metabolic tissues such as liver, gastrointestinal (GI) mucosal cell, lung, GI fluids, systemic circulation, extracellular fluid compartments, digestive fluids, blood, and any combination thereof.

It is another object of the present invention to provide the method as defined in any of the above, comprising an additional step of selecting the pro-drug from the group consisting of implants, nanoparticles, high-Z nanomaterials, gold nanoparticles, liposomes, pegylated liposomal formulation, encapsulating vehicle, immunoliposomes, peptide vectors, viral vectors, carrier mediated transporters, nanocarriers, nanospheres, nanocapsules, micelles, polymeric micelles, vesicles, polymers, drug conjugates, and any combination thereof.

It is another object of the present invention to provide the method as defined in any of the above, comprising an additional step of providing the pro-drug with at least one carrier or delivery vehicle selected from the group consisting of implants, nanoparticles, high-Z nanomaterials, gold nanoparticles, liposomes, pegylated liposomal formulation, encapsulating vehicle immunoliposomes, peptide vectors, viral vectors, carrier mediated transporters, nanocarriers, nanospheres, nanocapsules, micelles, polymeric micelles, vesicles, polymers, drug conjugates, and any combination thereof.

It is another object of the present invention to provide the method as defined in any of the above, comprising an additional step of encapsulating said drug or prodrug in an inactive configuration, further wherein said method comprises an additional step of activating said drug or pro-drug by decapsulation thereby providing the active drug.

It is another object of the present invention to provide the method as defined in any of the above, comprising an additional step of providing the pro-drug with poly(butyl) cyanoacrylate (PBCA), Tween-80, apolipoprotein E, lipoprotein, and any combination thereof.

It is another object of the present invention to provide the method as defined in any of the above, comprising an additional step of encasing the pro-drug in a carrier or vehicle.

It is another object of the present invention to provide the method as defined in any of the above, comprising an additional step of tagging or attaching the pro-drug with an antibody or a ligand.

It is another object of the present invention to provide the method as defined in any of the above, comprising an additional step of tagging or attaching the carrier or vehicle with an antibody or a ligand.

It is another object of the present invention to provide the method as defined in any of the above, comprising an additional step of linking the pro-drug with peptide vectors or viral vectors.

It is another object of the present invention to provide the method as defined in any of the above, comprising an additional step of providing the pro-drug with substrates for transporters.

It is another object of the present invention to provide the method as defined in any of the above, comprising an additional step of providing the pro-drug with substrates for transporters selected from the group consisting of influx transporters, efflux transporters, amino acid transporters, and any combination thereof.

It is another object of the present invention to provide the method as defined in any of the above, comprising an additional step of activating the pro-drug thereby targeting the active drug to a target tissue or cell or receptor.

It is another object of the present invention to provide the method as defined in any of the above, comprising an additional step of activating the pro-drug by a mechanism selected from the group consisting of decapsulation, encapsulation, oligomerization, polymerization, monomerization, cleavage, binding to a ligand, enzyme activation, chemical modification, radiolysis, excitation, formation of radicals, deprotonation, isomerization, reduction, oxidation, Enhanced Permeability and Retention (EPR) effect, and any combination thereof.

It is another object of the present invention to provide the method as defined in any of the above, comprising an additional step of enhancing drug delivery across the Blood Brain Barrier (BBB) prior, after, during or combinations thereof, administering the pro-drug or activating the pro-drug.

It is another object of the present invention to provide the method as defined in any of the above, comprising an additional step of enhancing drug delivery across the BBB by at least one mechanism selected from the group consisting of: radiotherapy or X-ray irradiation, administering inhibitors of BBB transporters, disrupting the BBB, providing the pro-drug with substrates for influx transporters mediating endogenous substrate transport from the circulation into the parenchyma or central nervous system (CNS), and any combination thereof.

It is another object of the present invention to provide the method as defined in any of the above, comprising an additional step of selecting the BBB transporters from the group consisting of multidrug resistance (MDR) proteins, ATP-binding cassette (ABC) transporter proteins, P-glycoproteins (ABCB1), multidrug resistance protein-1 MRP-1 (ABCC1), multidrug resistance protein-2 MRP-2 (ABCC2), breast cancer resistance protein BCRP (ABCG2), and any combination thereof.

It is another object of the present invention to provide the method as defined in any of the above, comprising an additional step of disrupting the BBB by at least one mechanism or agent selected from the group consisting of using hypertonic solutions such as mannitol, synthetic analogues such as receptor-mediated pemieabilizer RMP-7, modulators, and any combination thereof.

It is another object of the present invention to provide the method as defined in any of the above, comprising an additional step of treating a disease, especially cancer, tumour or proliferative disease comprising benign, pre-malignant, or malignant neoplasm, brain and central nervous system (CNS) tumors, bladder cancer, breast cancer, cervical cancer, colorectal cancer, esophageal cancer, liver cancer, ovarian epithelial cancer, pancreatic cancer, pituitary tumour, prostate cancer, rectal cancer, kidney cancer, small intestine cancer, urine sarcoma, vaginal cancer.

It is another object of the present invention to provide the method as defined in any of the above, comprising an additional step of designing the pro-drug so as to increase the bioavailability of antitumor drugs.

It is another object of the present invention to provide the method as defined in any of the above, comprising an additional step of designing the pro-drug so as to increase the local delivery of antitumor drugs.

It is another object of the present invention to provide the method as defined in any of the above, comprising additional steps of administering the pro-drug to the subject parenterally, intramuscularly, intradermally, topically, orally, intravenously, by injection, by infusion, by an implant, or by any combination thereof.

It is another object of the present invention to provide the method as defined in any of the above, wherein the photon dosage at the target site complies with the American College of Radiology (ACR), American Society of Radiologic Technologists (ASRT), American Society for Radiation Oncology (ASTRO) guidelines or any other treatment or safety guideline.

In an X-ray system configured for providing X-ray exposure to a target volume, it is another object of the present invention to provide the method as defined in any of the above, comprising additional steps of distributing the exposure over the target volume in a substantially uniform manner.

In an X-ray system configured for providing X-ray exposure to a target volume; it is another object of the present invention to provide the method as defined in any of the above, comprising additional steps of: (a) providing an X-ray beam; (b) providing at least one focusing lens configured for focusing radiation emitted by the beam, the lens being axially symmetric; the lens comprising crystal lens elements longitudinally arranged for Bragg X-ray diffraction of the radiation; (c) emitting X-ray radiation; and, (d) focusing the emitted radiation by the focusing lens within the target volume; wherein the radiation is emitted by an extendable aperture of a variable shape of the beam; the radiation is converted into a substantially uniform converging X-ray beam of a controllable waist size comparable with a size of the target volume, sufficient to convert the pro-drug to an active drug, whilst the X-ray photon dosage at the target site is higher than the X-ray photon dosage at an adjacent non target site.

It is another object of the present invention to provide a method for activating a pro-drug in vivo, comprising the steps of: (a) administering a pro-drug to a subject; (b) locating a target site at which has been at least partially dosed with a predetermined concentration of an enzymatic or chemical entity associated with the activation of the pro-drug; and (c) exposing the target site to X-ray radiation; wherein the step of exposing the target site to X-ray radiation is characterized by providing a converging X-ray of a controllable waist, substantially uniform at the target site, sufficient to convert the pro-drug to an active drug, whilst the X-ray photon dosage at the target site is higher than the X-ray photon dosage at an adjacent non target site.

It is another object of the present invention to provide a method for activating a biological reaction in vivo, comprising the steps of: (a) administering to a subject an enzymatic or chemical entity associated with the activation of the biological reaction; (b) locating a target site which has been at least partially dosed with a predetermined concentration of the enzymatic or chemical entity; and (c) exposing the target site to X-ray radiation; wherein the step of exposing the target site to X-ray radiation is characterized by providing a converging X-ray of a controllable waist, substantially uniform at the target site, sufficient to convert the pro-drug to an active drug, whilst the X-ray photon dosage at the target site is higher than the X-ray photon dosage at an adjacent non target site.

It is another object of the present invention to provide a method for activating a pro-drug in vivo, comprising the steps of: (a) administering to the subject a pro-drug at a predetermined concentration; (b) administering to the subject an enzymatic or chemical entity associated with the activation of the pro-drug at a predetermined concentration; (c) locating a target site which has been at least partially dosed with a predetermined concentration of the enzymatic or chemical entity associated with the activation of the pro-drug; and (d) exposing the target site to X-ray radiation; wherein the step of exposing the target site to X-ray radiation is characterized by providing a converging X-ray of a controllable waist, substantially uniform at the target site, sufficient to convert the pro-drug to an active drug, whilst the X-ray photon dosage at the target site is higher than the X-ray photon dosage at an adjacent non target site.

It is another object of the present invention to provide a protocol for activating a pro-drug in vivo comprising the steps of: (a) administering a pro-drug to a subject; (b) locating a target site which has been at least partially dosed with the pro-drug at a predetermined concentration; and (c) exposing the target site to X-ray radiation at predetermined doses and/or periodicities; wherein the step of exposing the target site to X-ray radiation is characterized by providing a converging X-ray of a controllable waist, substantially uniform at the target site, sufficient to convert the pro-drug to an active drug, whilst the X-ray photon dosage at the target site is higher than the X-ray photon dosage at an adjacent non target site.

It is another object of the present invention to provide a protocol for treating a cancerous, tumour or proliferative diseases in a subject comprising the steps of (a) administering a pro-drug to a subject; (b) locating a target site which has been at least partially dosed with the pro-drug at a predetermined concentration; and (c) exposing the target site to an X-ray administering protocol comprising a cell killing mode and a pro-drug-activating mode; wherein the step of exposing the target site to X-ray radiation is characterized by providing a converging X-ray of a controllable waist, substantially uniform at the target site, sufficient to convert the pro-drug to an active drug, whilst the X-ray photon dosage at the target site is higher than the X-ray photon dosage at an adjacent non target site.

It is another object of the present invention to provide the protocol as defined in any of the above, comprising additional steps of providing the X-ray administering protocol modes simultaneously, interchangeably or sequentially.

It is another object of the present invention to provide a system for activating a pro-drug in vivo comprising: (a) a pro-drug administered to a subject at a predetermined concentration; and (b) X-ray emitting means for emitting photon energy to a target site which has been at least partially dosed with the pro-drug at a predetermined concentration; wherein the X-ray emitting means is characterized by the ability to provide a substantially uniform converging X-ray of a controllable waist at the target site, sufficient to convert the pro-drug to an active drug, whilst the X-ray photon dosage at the target site is higher than the X-ray photon dosage at an adjacent non target site.

It is another object of the present invention to provide the system as defined in any of the above, wherein the pro-drug is administered to the subject in an effective dosage.

It is another object of the present invention to provide the system as defined in any of the above, wherein the X-ray emitting means are configured for providing X-ray exposure to a target volume, the X-ray irradiating means comprising an X-ray beam and at least one focusing lens wherein the exposure is distributed over a volume of the target in a substantially uniform manner.

It is another object of the present invention to provide the system as defined in any of the above, wherein the X-ray emitting means comprising: (a) an X-ray emitting beam; and, (b) at least one focusing lens configured for focusing radiation emitted by the beam, the lens being axially symmetric; the lens comprising Bragg-type lens elements longitudinally arranged for Bragg X-ray diffraction of the radiation; wherein an emitting aperture of a variable shape of the beam is extendable such that the lens provides a substantially uniform converging X-ray beam of a controllable waist size comparable with dimensions of the target volume.

It is another object of the present invention to provide the system as defined in any of the above, useful for treating a disease, especially cancer, tumor or proliferative disease selected from the group comprising benign, pre-malignant, or malignant neoplasm, brain and central nervous system (CNS) tumors, bladder cancer, breast cancer, cervical cancer, colorectal cancer, esophageal cancer, liver cancer, ovarian epithelial cancer, pancreatic cancer, pituitary tumour, prostate cancer, rectal cancer, kidney cancer, small intestine cancer, urine sarcoma, vaginal cancer.

It is another object of the present invention to provide a pro-drug predesigned to be converted to an active drug in situ upon exposure to X-ray radiation, wherein the exposure to X-ray radiation is characterized by the ability to provide a substantially uniform converging X-ray of a controllable waist at the target site, sufficient to convert the pro-drug to an active drug, whilst the X-ray photon dosage at the target site is higher than the X-ray photon dosage at an adjacent non target site.

It is another object of the present invention vide an active drug produced in situ from a pro-drug, the pro-drug is predesigned to be converted to an active drug at a target site upon exposure to X-ray radiation; the exposure to X-ray radiation is characterized by the ability to provide a converging X-ray of a controllable waist, substantially uniform at the target site, sufficient to convert the pro-drug to an active drug, whilst the X-ray photon dosage at the target site is higher than the X-ray photon dosage at an adjacent non target site.

It is another object of the present invention to provide an enzyme or chemical entity associated with converting a pro-drug to an active drug, wherein the enzyme or chemical entity is predesigned to be activated in situ upon exposure to X-ray radiation, wherein the exposure to X-ray radiation is characterized by the ability to provide a substantially uniform converging X-ray of a controllable waist at the target site, sufficient to convert the pro-drug to an active drug, whilst the X-ray photon dosage at the target site is higher than the X-ray photon dosage at an adjacent non target site.

It is another object of the present invention to provide a use of an X-ray system as defined in any of the above to activate a pro-drug in vivo.

It is another object of the present invention to provide the use of an X-ray system as defined in any of the above to treat a disease, especially a cancerous, tumor or proliferative disease.

It is another object of the present invention to provide a pro-drug comprising at least one first component and at least one second component, wherein at least one of the components is predesigned so as to be activable at an in vivo target site upon exposure to a converging X-ray of a controllable waist, substantially uniform at the target site, sufficient to activate at least the first component thereby enabling a direct or indirect interaction with at least the second component potentially convertable to an active drug, whilst the X-ray photon dosage at the target site is higher than the X-ray photon dosage at an adjacent non target site.

It is another object of the present invention to provide the pro-drug as defined in any of the above, wherein the interaction of at least one first component and at least one second component provides the active drug at a higher potency, efficacy, affinity, local concentration, functionality or any combination thereof, than is provided by in vivo interaction of at least one first component and at least one second component absent of the exposure to the converging X-ray.

It is another object of the present invention to provide a system useful for treating a disease comprising at least one first pro-drug and at least one second pro-drug, wherein at least one of the pro-drugs is predesigned so as to be activable upon exposure to a converging X-ray of a controllable waist, substantially uniform at the in vivo target site, sufficient to activate at least the first pro-drug, the system of at least one first pro-drug and at least one second pro-drug, upon administration to a subject, provides a greater than additive therapeutic effect than if at least one of the pro-drugs were administered absent of the exposure to the converging X-ray.

It is another object of the present invention to provide a system as defined in any of the above, wherein at least one first pro-drug and at least one second pro-drug are administered contemporaneously.

It is another object of the present invention to provide a system as defined in any of the above, wherein at least one first pro-drug and at least one second pro-drug are administered in a sequential manner.

BRIEF DESCRIPTION OF THE FIGURES

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention. The present invention may be practiced according to the claims without some or all of these specific details. For the purpose of clarity, technical material that is known in the technical fields related to the invention has not been described in detail so that the present invention is not unnecessarily obscured. The present invention provides a method for activating a pro-drug in a specific target site with increased effectiveness and reduced adverse effects by using a converging x-ray beam of a controllable waist.

DETAILED DESCRIPTION OF THE PREFERRED EMBODIMENTS

Figure 1:
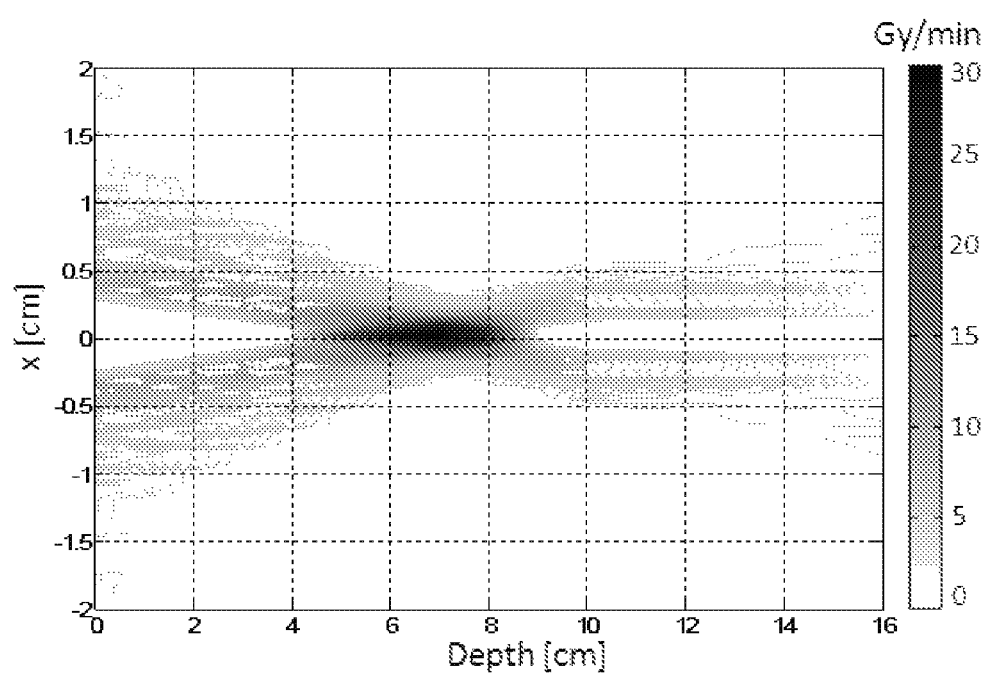
FIG. 1 presents an exemplary graphic representation of a converging beam profile as an embodiment of the present invention.

The following description is provided, alongside all chapters of the present invention, so as to enable any person skilled in the art to make use of the invention and set forth the best modes contemplated by the inventor of carrying out this invention. Various modifications, however, will remain apparent to those skilled in the art, since the generic principles of the present invention is defined to specifically provide a method for activating a pro-drug in a specific target site with increased effectiveness and reduced adverse effects by using a converging x-ray beam of a controllable waist.

As used herein, the term "plurality" refers in a non-limiting manner to any integer equal to or greater than 1.

The term "about" refers herein to a value being ±25% of the defined measure.

The term "approximately" refers herein a value being ±25% of the defined measure.

The term "pro-drug" refers hereinafter to a medication that is initially administered to the body in an inactive, or less than fully active form, and then becomes converted to its active form in a specific target site by irradiating it with high-energy ionizing radiation. It is further included within the scope of the invention that the term pro-drug relates to a prodrug and/or drug that is encapsulated or otherwise attached to a delivery agent or vehicle such as a particle or a liposome, preventing it from being active. The exposure of the delivery vehicle, at a predetermined site, to irradiation by X-ray i.e. to a converging X-ray beam, provides the active drug in a specific and controllable manner, for example by decapsulation of the delivery vehicle, or by any other mechanism enabling the release of the active drug by the ionizing radiation at a controlled manner.

Examples of delivery vehicles included within the scope of the present invention may comprise: implants, nanoparticles, for example gold nanoparticles for increasing the contrast effect in radiotherapy treatment (McMahon et al, 2008, Phys. Med Biol. 53:5635-5631 and Hainfeld et al. 2004, Phys. Med Biol. 49; are both incorporated here by reference as embodiments of the present invention), liposomes such as electrostatic liposome encapsulation vehicles (i.e. U.S. Pat. No. 6,559,129 is incorporated herein by reference as an embodiment of the present invention), lipophilic moieties, encapsulating vehicle, pegylated liposomal formulation, immunoliposomes, peptide vectors, viral vectors or delivery vehicles, carrier mediated transporters, nanocarriers, nanospheres, nanocapsules, micelles, polymeric micelles, vesicles, polymers, drug conjugates, and any other conventional drug delivery vehicle and any combination thereof.

It is further within the scope of the present invention, wherein high density and atomic number (Z) materials, typically involving a gradient from high-Z (usually tantalum) through successively lower-Z elements such as tin, steel, and copper, may be used as contrast agents, when the effective atomic number (Z) is different from that of the surrounding tissue. The contrast produced by a difference in chemical composition (atomic number) is sensitive to photon energy and the spectrum of the x-ray beam.

It is herein acknowledged that most materials that produce high contrast with respect to soft tissue differ from the soft tissue in both physical density and atomic number. The high-Z materials (e.g. gold particles) effectively scatter protons and electrons. It is further noted that the high-Z nanomaterials may be delivered in a delivery vehicle such as viral vectors or any other particle or nanoparticle, prior, during or after administering the prodrug to a subject, subjected to the X-ray converging beam protocol and/or radiotherapy protocol. The aforementioned therapy method may be used to increase specificity and efficacy in chemotherapeutic treatment of cancer or tumor diseases, as well as other ailments.

According to a further aspect of the invention, the delivery vehicle comprises any conventionally used biocompatible material, e.g. a synthetic or natural material designed to function in intimate contact with living tissue. In certain embodiments, biocompatible materials are intended to interface with biological systems.

The term "target site" refers herein after to a treatment site or treatment volume of a region of interest in the body, including regions, sites or volumes (i.e. cells or tissues or organs) proximate to said region of interest.

The term "X-ray radiation" refers hereinafter to a form of electromagnetic radiation having a photon energy range of about 100 eV to about 500 keV. More specifically, the term relates to orthovoltage x-ray radiation (deep x-ray) which is produced by X-ray generators operating at voltages in the 200-500 kV range, and therefore having energy of up to 500 keV range.

The term "converging x-ray beam" or "converging X-ray" refers hereinafter to a beam whose rays start from separate spread locations and converge to a common location, site or volume—the focal location—at the focal distance. It can be a point-focal point, or small cross section area at the focal plane or a target volume or a target site in the body. Thus, the average radiation flux cross section area density is increasing along the longitudinal axis until reaching a maximum related to the focal location or target site or target volume. Beyond the focal distance the rays diverge. It is well within the scope, wherein the invention may encompass any converging X-ray mechanism or technique or method available or published, for example, Vo, Nghia T. et al. Applied Physics Letters November 2012 (Volume: 101, Issue: 22), U.S. Pat. Nos. 8,416,921, 8,406,374, WO2012023141A1 incorporated herein by reference.

The term "waist" hereinafter refers to a contour in a transversal cross section of the X-ray beam wherein beam intensity within the aforesaid contour does not fall below 50% of the peak intensity.

The term "uniform exposure" hereinafter refers to exposure transversal distribution of the X-ray beam within the waist which does not fall below 50% of the peak exposure.

The term "radiotherapy" refers hereinafter to the medical use of ionizing radiation, generally as part of cancer treatment, to control or kill malignant cells. It may also be used as part of adjuvant therapy, to prevent tumor recurrence after surgery to remove a primary malignant tumor. Radiation therapy may be synergistic with chemotherapy, and may be used before, during, and after chemotherapy in susceptible cancers. According one embodiment, radiotherapy relates to a mode of treatment wherein the therapeutic dose, totaling between 20 and 80 Gy, can be administered in more than one fraction, usually in a number of fractions, with a resting duration of between several hours to several days between fractions, for example in more than 10 fractions.

The term "radiosurgery" refers hereinafter to a mode of treatment, wherein a therapeutic dose of radiation is delivered to a region of treatment. The therapeutic dose, totaling between 20 and 80 Gy, can be administered in one fraction, or in a small number of fractions, with a resting duration of few hours, for example in less than 10 fractions given within a short period of time, for example 6 hours interval between fractions.

The term "blood brain barrier (BBB)" refers hereinafter to a separation of circulating blood from the brain extracellular fluid in the central nervous system. It occurs along all capillaries and consists of tight junctions around the capillaries that do not exist in normal circulation. Endothelial cells restrict the diffusion of microscopic objects and large or hydrophilic molecules into the cerebrospinal fluid, while allowing the diffusion of small hydrophobic molecules. Cells of the barrier actively transport metabolic products such as glucose across the barrier with specific proteins. It is within the scope of the present invention, wherein the system and method of the present invention are designed to encompass means and methods for enhancing and improving drug delivery across the Blood Brain Barrier (BBB) prior, after, during or combinations thereof, administering the pro-drug or activating the pro-drug. Examples of mechanisms used to enhance drug delivery across the BBB include radiotherapy or exposure to ionizing radiation, administering inhibitors of BBB transporters, disrupting the BBB, providing the pro-drug with substrates for influx transporters mediating endogenous substrate transport from the circulation into the parenchyma or central nervous system (CNS), and any combination thereof or any other mechanism or means conventionally known to enhance the BBB permeability.

The present invention provides a method for activating a pro-drug in viva comprising the steps of: (a) administering a pro-drug to a subject; (b) locating a target site which has been at least partially dosed with the pro-drug at a predetermined concentration; and (c) exposing the target site to X-ray radiation; wherein the step of exposing the target site to X-ray radiation is characterized by providing a converging X-ray of a controllable waist, substantially uniform at the target site, sufficient to convert the pro-drug to an active drug, whilst the X-ray photon dosage at the target site is higher than the X-ray photon dosage at an adjacent non target site.

In another embodiment of the invention, the method as defined above comprises additional steps of exposing the target site to X-ray characterized by photon energy of up to 500 keV, more particularly up to 250 keV.

It is thus a main aspect of the invention to provide means and methods to activate a prodrug into an active drug in a specific and selective manner at the target site. The activation of the prodrug is herein unexpectedly performed by using a converging X-ray mechanism or apparatus enabling improved efficacy of the drug therapy and enhanced specificity to the desired target tissue, while having reduced side and adverts effects at proximate or other healthy tissues or cells. One advantage of using the method and system disclosed interalia is improved delivery of the drug to the target site. In other words, by activating the prodrug in a controlled manner, i.e. at the target site, with minimal effects to healthy tissues or cells, an incensed amound of the drug can reach the desired target site and thus an improved efficacy of the drug is obtained. It is herein further acknowledged that by improving the specificity of the drug to the target site, the concentration of the drug at the target site is increased, less adverse effects are caused by the drug and thus higher concentrations of the drug can be administered, which lead to enhanced efficacy.

An example of an application of the disclosed system and method is for treatment of tumor or cancerous diseases. The common treatment of cancerous diseases is by the administration of chemotherapeutic agents. By using the present invention, significant advantage of existing chemotherapy treatments are achieved, with less side effects by the anticancer agent to the patient and improved efficacy of the administered drug.

It is further within the scope that the prodrug may be administered to a subject by different methods. Systemic and non-systemic methods of administration are suitable. Such methods include an injection (intramuscular, intraarterial, intraperitoneal, intravenous, intratumoral or other site-specific injection, intrathecal, inhalatories, oral administration, and topical methods or by releasing the drug from implants.

In a specific embodiment of the invention, biochemical molecules such as oligonucleotides, antisense oligonucleotides (e.g. antisense ODN therapeutics), or proteins e.g. that correspond to oncogenes can be used as prodrugs or further used to enhance the sensitivity of tumor cells (radiosensitizer) to radiotherapy, or enhance specificity of the drug, thereby enhancing efficacy. Without wishing to be bound thereby, it is theorized that such molecules may render tumor cells more susceptible to lysis or apoptosis processes and thus increase the effectively of the treatment. Such biochemical molecules or prodrugs will preferably be administered in an encapsulated form, i.e. liposome encapsulated form, prior, concurrent, or shortly after ionizing radiation therapy.

According to a main aspect of the invention, the activation of a pro-drug in a specific target site is unexpectedly achieved by using a converging x-ray beam. Thus, the present invention may enable use of lower dosages of radiation at the target volume or site than previous therapies thereby proving an enhanced effectiveness of the drug with reduced adverse effects associated with the irradiation protocol to healthy tissues or cells exposed to the X-ray radiation.

The present invention encompasses any converging X-ray technology, with reference to the following examples, Reference is now made to FIG. 1, presenting an exemplary graphic representation of a converging beam profile as an embodiment of the present invention. In this embodiment, the convergent of the X-ray beam is made by a set of reflecting lens. This figure shows the dose distribution through the body after exposure to a converging single "shot" x-ray dose, having photon energy of 60 keV. More specifically, the graphic representation describes a cross section view of the dose distribution along the depth axis within the body, under the skin surface (defined by Depth axis in FIG. 1), and along the skin surface exposure zone (defined by x [cm] axis in FIG. 1), As can be seen, the converging beam profile is characterized by an axial symmetry with a maximal absorbed dose rate (Gy/min) at a depth ranging between about 6 cm to about 8 cm, i.e. at the focal site or volume inside the body.

Figure 2:
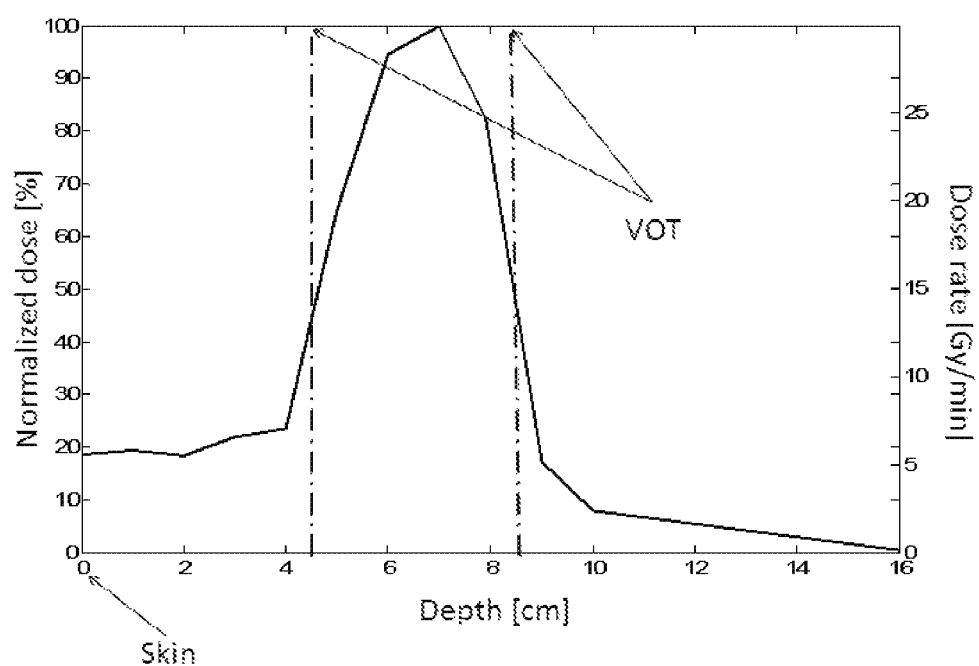
FIG. 2 presents an exemplary graphic representation of the Percentage Dose Depth (PDD) distribution of a converging beam profile of a single "shot", as an embodiment of the present invention.

Reference is now made to FIG. 2, presenting an exemplary graphic representation of the Percentage Dose Depth (PDD) distribution profile of a single exposure of a converging beam (i.e. applying a single "shot" of a converging beam) as an embodiment of the present invention.

It is herein acknowledged that the term "percentage depth dose" or "PDD" relates herein after to the absorbed dose deposited by a radiation beam into a medium as it varies with depth along the axis of the beam. The dose values are divided by the maximum dose (e.g. referred to as dmax), yielding a plot in terms of percentage or fraction of the maximum dose.

In this embodiment, the normalized dose distribution (defined by percentage relative to the maximal dose) along the depth axis under the skin surface, is described. The results shown in this figure clearly show that by exposure of the body to a single shot x-ray converging beam, a maximal dose is specifically achieved at focal site or volume of treatment (VOT) (about 6 to 8 cm depth under the skin surface), with substantially and significantly reduced radiation doses at tissues or cells preceding or following the focal or target tissue nor in tissues surrounding the focal site or volume. Thus it is herein demonstrated that by using the method and system of the present invention, maximal pro-drug activation effectiveness is achieved at the target site, with substantially reduced adverts effects such as radiation damage to healthy surrounding tissues.

Figure 3:
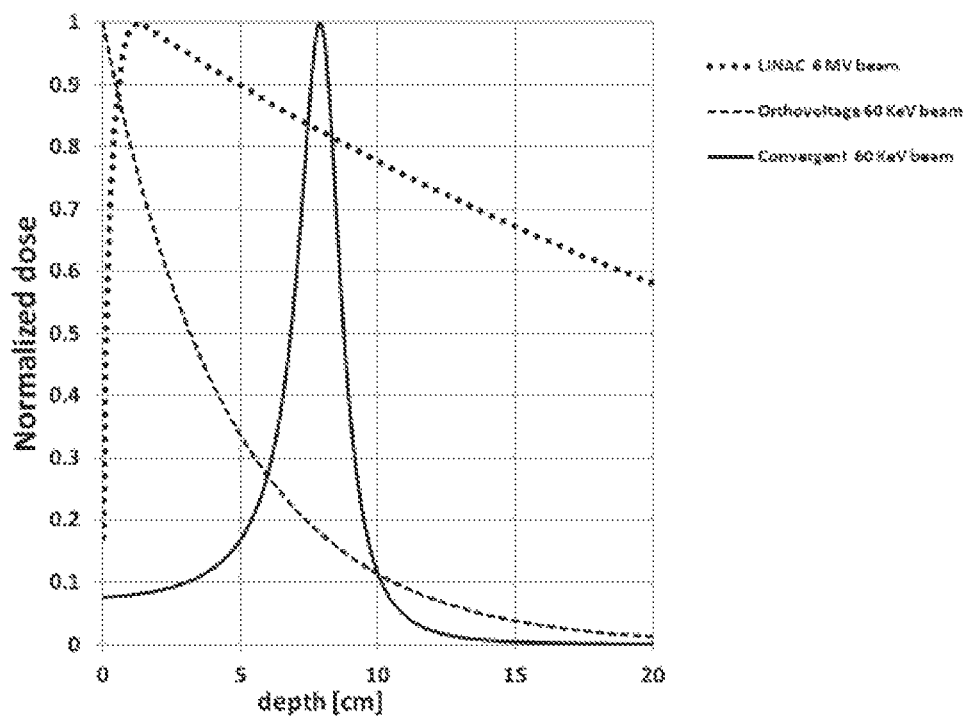
FIG. 3 presents an exemplary graphic representation of relative dose fraction as function of depth in soft tissues, of a single exposure of a converging beam, as compared to linear particle accelerator (LINAC) beam and orthovoltage beam.

Reference is now made to FIG. 3 presenting an exemplary graphic representation of relative dose fraction as function of depth in soft tissues, of a converging beam, as compared to other beam types. This embodiment shows a comparison of Percentage Dose Depth (PDD) curve of a converging 60 keV beam relative to orthovoltage 60 key beam and linear particle accelerator (LINAC) 6MV beam. For the converging beam, the parameters applied in the experiment exemplified in the graphic representation of FIG. 3 are the following: tube power of about 100 W, half angle of about 15 deg., focal depth of about 8 cm and focal spread diameter of about 5 mm.

As can be seen, the usage of a converging beam produces maximal dose pick specifically at the focal or target site (i.e. about 8 cm depth). In contrast, single exposure of other types of beams, demonstrate a significantly reduced absorbed dose at the focal site and elevated absorbed doses at healthy, non-focal tissues proximally to the beam source, i.e. at the skin surface or in non-target tissues proximal to the skin surface (up to 2 cm depth).

In summary, the above results show that by exposure to a single shot converging x-ray beam, as opposed to other beam types, a maximal absorbed dose at the focal or target treatment site located inside the body is achieved. The high radiation dose, specifically focused at the treatment site, is herein unexpectedly used to activate a prodrug in a controllable and effective manner, with significantly reduced adverse effects to regions surrounding the tissue or region of interest. In this way higher efficacy of the drug administered, e.g. chemotherapeutic drug, is achieved with less side effects. Thus it is herein demonstrated that the present invention provides means and methods for activating a prodrug in vivo by exposing the target site to X-ray radiation and more specifically, by providing a converging X-ray beam substantially uniform at said target site, sufficient to convert said pro-drug to an active drug, whilst the X-ray dosage at the target site is higher than the X-ray dosage at an adjacent non target site.

It is according to one embodiment of the invention, wherein a method for activating a pro-drug in vivo comprising the steps of (a) administering a pro-drug to a subject; (b) locating a target site which has been at least partially dosed with the pro-drug at a predetermined concentration; and (c) exposing the target site to X-ray radiation; wherein the step of exposing the target site to X-ray radiation is characterized by providing a converging X-ray of a controllable waist, substantially uniform at the target site, sufficient to convert the pro-drug to an active drug, whilst the X-ray photon dosage at the target site is higher than the X-ray photon dosage at an adjacent non target site.

In yet another embodiment of the invention, the method as defined in any of the above comprising additional steps of exposing the target site to X-ray characterized by photon energy of up to 500 keV and more particularly up to 250 keV.

In yet another embodiment of the invention, the method as defined in any of the above comprising additional steps of exposing the target site to X-ray characterized by photon energy in the range of between about 30 keV and about 180 keV.

I In yet another embodiment of the invention, the method as defined in any of the above comprising additional steps of providing an in vivo reservoir of pro-drug and exposing the reservoir of pro-drug to X-ray in a predetermined manner to convert a predetermined quantity of the pro-drug to the active drug.

In yet another embodiment of the invention, the method as defined in any of the above comprising additional steps of exposing the target site to an X-ray administering protocol comprising a cell killing mode and a pro-drug-activating mode.

In yet another embodiment of the invention, the method as defined in any of the above comprising additional steps of providing the X-ray administering protocol modes simultaneously, interchangeably or sequentially.

In yet another embodiment of the invention, the method as defined in any of the above comprising an additional step of exposing the target site to X-ray doses in the range of between about 20 Gy to about 80 Gy, or to any other dosing protocol.

In yet another embodiment of the invention, the method as defined in any of the above comprising an additional step of exposing the target site to X-ray doses in the range of between about 20 Gy to about 80 Gy, provided in 1.8 to 4 Gy fractions, or in any other dose fractionating protocol.

In yet another embodiment of the invention, the method as defined in any of the above comprising an additional step of exposing the target site to a radiotherapy protocol or to a radiosurgery protocol or to a combination thereof.

In yet another embodiment of the invention, the method as defined in any of the above comprising an additional step of exposing the target site to X-ray radiation after or during or a combination thereof, administering the pro-drug.

In yet another embodiment of the invention, the method as defined in any of the above comprising an additional step of designing the pro-drug so as to be activated after an enzymatic or chemical reaction.

In yet another embodiment of the invention, the method as defined in any of the above comprising an additional step of activating the enzymatic or chemical reaction by exposure to X-ray radiation; wherein the step of exposure to X-ray radiation is characterized by providing a converging X-ray of a controllable waist, substantially uniform at the target site, sufficient to convert the pro-drug to an active drug, whilst the X-ray photon dosage at the target site is higher than the X-ray photon dosage at an adjacent non target site.

In yet another embodiment of the invention, the method as defined in any of the above comprising an additional step of selecting the pro-drug from the group consisting of oligonucleotides, antisense oligonucleotides, lipids, chemical derivatives, biological molecules or derivatives thereof, precursors, analogs, antibodies, genes, enzymes, amino acids, proteins, metabolites, enantiomers, glycoproteins, lipoproteins, viral vectors, and any combination thereof.

In yet another embodiment of the invention, the method as defined in any of the above comprising an additional step of selecting the pro-drug from the group of types based on bioactivation site, consisting of intracellular site, extracellular site, and a combination thereof.

In yet another embodiment of the invention, the method as defined in any of the above comprising an additional step of selecting the pro-drug from the group of types based on tissue location of bioactivation, consisting of therapeutic target tissues or cells, metabolic tissues such as liver, gastrointestinal (GI) mucosal cell, lung, GI fluids, systemic circulation, extracellular fluid compartments, digestive fluids, blood, and any combination thereof.

In yet another embodiment of the invention, the method as defined in any of the above comprising an additional step of selecting the pro-drug from the group consisting of implants, nanoparticles, high-Z nanomaterials, gold nanoparticles, liposomes, pegylated liposomal formulation, encapsulating vehicle, immunoliposomes, peptide vectors, viral vectors, carrier mediated transporters, nanocarriers, nanospheres, nanocapsules, micelles, polymeric micelles, vesicles, polymers, drug conjugates, and any combination thereof.

In yet another embodiment of the invention, the drug or prodrug is encapsulated in an inactive configuration further wherein said method comprises an additional step of activating said drug or pro-drug by decapsulation thereby providing the active drug.

In yet another embodiment of the invention, the method as defined in any of the above comprising an additional step of providing the pro-drug with at least one carrier or vehicle selected from the group consisting of implants, nanoparticles, high-Z nanomaterials, gold nanoparticles, liposomes, pegylatedliposomal formulation, encapsulated vehicle, immunoliposomes, peptide vectors, viral vectors, carrier mediated transporters, nanocarriers, nanospheres, nanocapsules, micelles, polymeric micelles, vesicles, polymers, drug conjugates, and any combination thereof.

In yet another embodiment of the invention, the method as defined in any of the above comprising an additional step of providing the pro-drug with poly(butyl)cyanoacrylate (PICA), Tween-80, apolipoprotein E, lipoprotein, and any combination thereof.

In yet another embodiment of the invention, the method as defined in any of the above comprising an additional step of encasing the pro-drug in a carrier or vehicle.

In yet another embodiment of the invention, the method as defined in any of the above comprising an additional step of tagging or attaching the pro-drug with an antibody or a ligand.

In yet another embodiment of the invention, the method as defined in any of the above comprising an additional step of tagging or attaching the carrier or vehicle with an antibody or a ligand.

In yet another embodiment of the invention, the method as defined in any of the above comprising an additional step of linking the pro-drug with peptide vectors or viral vectors.

In yet another embodiment of the invention, the method as defined in any of the above comprising an additional step of providing the pro-drug with substrates for transporters.

In yet another embodiment of the invention, the method as defined in any of the above comprising an additional step of providing the pro-drug with substrates for transporters selected from the group consisting of influx transporters, efflux transporters, amino acid transporters, and any combination thereof.

In yet another embodiment of the invention, the method as defined in any of the above comprising an additional step of activating the pro-drug, thereby targeting the active drug to a target tissue or cell or receptor.

In yet another embodiment of the invention, the method as defined in any of the above comprising an additional step of activating the pro-drug by a mechanism selected from the group consisting of decapsulation, encapsulation, oligomerization, polymerization, monomerization, cleavage, binding to a ligand, enzyme activation, chemical modification, radiolysis, excitation, formation of radicals, deprotonation, isomerization, reduction, oxidation, Enhanced Permeability and Retention (EPR) effect, and any combination thereof.

In yet another embodiment of the invention, the method as defined in any of the above comprising an additional step of enhancing drug delivery across the Blood Brain Barrier (BBB) prior, after, during or combinations thereof, administering the pro-drug or activating the pro-drug.

In some of the embodiments in which the target site is the central nervous system, the administering of the pro-drug and the x-radiation is combined with enhancement of the drug delivery across the BBB. There are several means for improving drug delivery across the BBB. The most relevant method is radiation that disrupts the BBB. In this case the X-radiation can have a dual effect of activation of the pro-drug and increasing its delivery to the brain. Other methods for increasing the CNS penetration of chemotherapy agents include inhibition of BBB transporters and using hypotonic solutions such as mannitol.

In yet another embodiment of the invention, the method as defined in any of the above comprising an additional step of enhancing drug delivery across the BBB by at least one mechanism selected from the group consisting of radiotherapy or X-ray irradiation, administering inhibitors of BBB transporters, disrupting the BBB, providing the pro-drug with substrates for influx transporters mediating endogenous substrate transport from the circulation into the parenchyma or central nervous system (CNS), and any combination thereof.

In yet another embodiment of the invention, the method as defined in any of the above comprising an additional step of selecting the BBB transporters from the group consisting of multidrug resistance (MDR) proteins, ATP-binding cassette (ABC) transporter proteins, P-glycoproteins (ABCB1), multidrug resistance protein-1 MRP-1 (ABCC1), multidrug resistance protein-2 MRP-2 (ABCC2), breast cancer resistance protein BCRP (ABCG2), and any combination thereof.

In yet another embodiment of the invention, the method as defined in any of the above comprising an additional step of disrupting the BBB by at least one mechanism or agent selected from the group consisting of using hypertonic solutions such as mannitol, synthetic analogues such as receptor-mediated permeabilizer RMP-7, modulators, and any combination thereof.

In yet another embodiment of the invention, the method as defined in any of the above comprising an additional step of treating a disease, especially cancer, tumour or proliferative disease comprising benign, pre-malignant, or malignant neoplasm, brain and central nervous system (CNS) tumors, bladder cancer, breast cancer, cervical cancer, colorectal cancer, esophageal cancer, liver cancer, ovarian epithelial cancer, pancreatic cancer, pituitary tumour, prostate cancer, rectal cancer, kidney cancer, small intestine cancer, urine sarcoma, vaginal cancer.

In yet another embodiment of the invention, the method as defined in any of the above comprising an additional step of designing the pro-drug so as to increase the bioavailability of antitumor drugs.

In yet another embodiment of the invention, the method as defined in any of the above comprising an additional step of designing the pro-drug so as to increase the local delivery of antitumor drugs.

In yet another embodiment of the invention, the method as defined in any of the above comprising additional steps of administering the pro-drug to the subject parenterally, intramuscularly, intradermally, topically, orally, intravenously, by injection, by infusion, by an implant, or by any combination thereof.

In yet another embodiment of the invention, the photon dosage at the target site complies with the American College of Radiology (ACR), American Society of Radiologic Technologists (ASRT), American Society for Radiation Oncology (ASTRO) guidelines or any other treatment or safety guideline.

In yet another embodiment of the invention, an X-ray system configured for providing X-ray exposure to a target volume, comprising additional steps of distributing the exposure over the target volume in a substantially uniform manner.

In yet another embodiment of the invention, an X-ray system configured for providing X-ray exposure to a target volume, comprising additional steps of (a) providing an X-ray beam; (b) providing at least one focusing lens configured for focusing radiation emitted by the beam, the lens being axially symmetric; the lens comprising crystal lens elements longitudinally arranged for Bragg X-ray diffraction of the radiation; (c) emitting X-ray radiation; and, (d) focusing the emitted radiation by the focusing lens within the target volume; wherein the radiation is emitted by an extendable aperture of a variable shape of the beam; the radiation is converted into a substantially uniform converging X-ray beam of a controllable waist size comparable with a size of the target volume, sufficient to convert the pro-drug to an active drug, whilst the X-ray photon dosage at the target site is higher than the X-ray photon dosage at an adjacent non target site.

In yet another embodiment of the invention, a method for activating a pro-drug in vivo, comprising the steps of (a) administering a pro-drug to a subject; (b) locating a target site at which has been at least partially dosed with a predetermined concentration of an enzymatic or chemical entity associated with the activation of the pro-drug; and (c) exposing the target site to X-ray radiation; wherein the step of exposing the target site to X-ray radiation is characterized by providing a converging X-ray of a controllable waist, substantially uniform at the target site, sufficient to convert the pro-drug to an active drug, whilst the X-ray photon dosage at the target site is higher than the X-ray photon dosage at an adjacent non target site.

In yet another embodiment of the invention, a method for activating a biological reaction in vivo, comprising the steps of: (a) administering to a subject an enzymatic or chemical entity associated with the activation of the biological reaction; (b) locating a target site which has been at least partially dosed with a predetermined concentration of the enzymatic or chemical entity; and (c) exposing the target site to X-ray radiation; wherein the step of exposing the target site to X-ray radiation is characterized by providing a converging X-ray of a controllable waist, substantially uniform at the target site, sufficient to convert the pro-drug to an active drug, whilst the X-ray photon dosage at the target site is higher than the X-ray photon dosage at an adjacent non target site.

In yet another embodiment of the invention, a method for activating a pro-drug in vivo, comprising the steps of (a) administering to the subject a pro-drug at a predetermined concentration; (b) administering to the subject an enzymatic or chemical entity associated with the activation of the pro-drug at a predetermined concentration; (c) locating a target site which has been at least partially dosed with a predetermined concentration of the enzymatic or chemical entity associated with the activation of the pro-drug; and (d) exposing the target site to X-ray radiation; wherein the step of exposing the target site to X-ray radiation is characterized by providing a converging X-ray of a controllable waist, substantially uniform at the target site, sufficient to convert the pro-drug to an active drug, whilst the X-ray photon dosage at the target site is higher than the X-ray photon dosage at an adjacent non target site.

In yet another embodiment of the invention, a protocol for activating a pro-drug in vivo comprising the steps of (a) administering a pro-drug to a subject; (b) locating a target site which has been at least partially dosed with the pro-drug at a predetermined concentration; and (c) exposing the target site to X-ray radiation at predetermined doses and/or periodicities; wherein the step of exposing the target site to X-ray radiation is characterized by providing a converging X-ray of a controllable waist, substantially uniform at the target site, sufficient to convert the pro-drug to an active drug, whilst the X-ray photon dosage at the target site is higher than the X-ray photon dosage at an adjacent non target site.

In yet another embodiment of the invention; a protocol for treating a cancerous, tumour or proliferative diseases in a subject comprising the steps of (a) administering a pro-drug to a subject; (b) locating a target site which has been at least partially dosed with the pro-drug at a predetermined concentration; and (c) exposing the target site to an X-ray administering protocol comprising a cell killing mode and a pro-drug-activating mode; wherein the step of exposing the target site to X-ray radiation is characterized by providing a converging X-ray of a controllable waist, substantially uniform at the target site, sufficient to convert the pro-drug to an active drug, whilst the X-ray photon dosage at the target site is higher than the X-ray photon dosage at an adjacent non target site.

In yet another embodiment of the invention, comprising additional steps of providing the X-ray administering protocol modes simultaneously, interchangeably or sequentially.

In yet another embodiment of the invention, a system for activating a pro-drug in vivo comprising: (a) a pro-drug administered to a subject at a predetermined concentration; and (h) X-ray emitting means for emitting photon energy to a target site which has been at least partially dosed with the pro-drug at a predetermined concentration; wherein the X-ray emitting means is characterized by the ability to provide a substantially uniform converging X-ray of a controllable waist at the target site, sufficient to convert the pro-drug to an active drug, whilst the X-ray photon dosage at the target site is higher than the X-ray photon dosage at an adjacent non target site.

In yet another embodiment of the invention, wherein the pro-drug is administered to the subject in an effective dosage.

In yet another embodiment of the invention, wherein the X-ray emitting means are configured for providing X-ray exposure to a target volume, the X-ray irradiating means comprising an X-ray beam and at least one focusing lens wherein the exposure is distributed over a volume of the target in a substantially uniform manner.

In yet another embodiment of the invention, wherein the X-ray emitting means comprising: (a) an X-ray emitting beam; and, (b) at least one focusing lens configured for focusing radiation emitted by the beam, the lens being axially symmetric; the lens comprising Bragg-type lens elements longitudinally arranged for Bragg X-ray diffraction of the radiation; wherein an emitting aperture of a variable shape of the beam is extendable such that the lens provides a substantially uniform converging X-ray beam of a controllable waist size comparable with dimensions of the target volume.

In yet another embodiment of the invention a system as defined in any of the above, useful for treating a disease, especially cancer, tumor or proliferative disease selected from the group comprising benign, pre-malignant, or malignant neoplasm, brain and central nervous system (CNS) tumors, bladder cancer, breast cancer, cervical cancer, colorectal cancer, esophageal cancer, liver cancer, ovarian epithelial cancer, pancreatic cancer, pituitary tumour, prostate cancer, rectal cancer, kidney cancer, small intestine cancer, urine sarcoma, vaginal cancer.

In yet another embodiment of the invention a pro-drug predesigned to be converted to an active drug in situ upon exposure to X-ray radiation at photon energy of up to 500 keV, particularly up to 250 keV, wherein the exposure to X-ray radiation is characterized by the ability to provide a substantially uniform converging X-ray of a controllable waist at the target site, sufficient to convert the pro-drug to an active drug, whilst the X-ray photon dosage at the target site is higher than the X-ray photon dosage at an adjacent non target site.

In yet another embodiment of the invention an active drug produced in situ from a pro-drug, the pro-drug is predesigned to be converted to an active drug at a target site upon exposure to X-ray radiation at photon energy of up to 500 keV, particularly up to 250 keV; the exposure to X-ray radiation is characterized by the ability to provide a converging X-ray of a controllable waist, substantially uniform at the target site, sufficient to convert the pro-drug to an active drug, whilst the X-ray photon dosage at the target site is higher than the X-ray photon dosage at an adjacent non target site.

In yet another embodiment of the invention an enzyme or chemical entity associated with converting a pro-drug to an active drug, wherein the enzyme or chemical entity is predesigned to be activated in situ upon exposure to X-ray radiation at photon energy of up to 500 keV, particularly up to 250 keV, wherein the exposure to X-ray radiation is characterized by the ability to provide a substantially uniform converging X-ray of a controllable waist at the target site, sufficient to convert the pro-drug to an active drug, whilst the X-ray photon dosage at the target site is higher than the X-ray photon dosage at an adjacent non target site.

In yet another embodiment of the invention an X-ray system as defined in any of the above to activate a pro-drug in vivo.

In yet another embodiment of the invention a use of an X-ray system as defined in any of the above to treat a disease, especially a cancerous, tumor or proliferative disease.

In yet another embodiment of the invention a pro-drug comprising at least one first component and at least one second component, wherein at least one of the components is predesigned so as to be activable at an in vivo target site upon exposure to a converging X-ray of a controllable waist, substantially uniform at the target site, sufficient to activate at least the first component thereby enabling a direct or indirect interaction with at least the second component potentially convertable to an active drug, whilst the X-ray photon dosage at the target site is higher than the X-ray photon dosage at an adjacent non target site.

In yet another embodiment of the invention, wherein the interaction of at least one first component and at least one second component provides the active drug at a higher potency, efficacy, affinity, local concentration, functionality or any combination thereof, than is provided by in vivo interaction of at least one first component and at least one second component absent of the exposure to the converging X-ray.

In yet another embodiment of the invention a system useful for treating a disease comprising at least one first pro-drug and at least one second pro-drug, wherein at least one of the pro-drugs is predesigned so as to be activable upon exposure to a converging X-ray of a controllable waist, substantially uniform at the target site, sufficient to activate at least the first pro-drug, the system of at least one first pro-drug and at least one second pro-drug, upon administration to a subject, provides a greater than additive therapeutic effect than if at least one of the pro-drugs were administered absent of the exposure to the converging X-ray.

In yet another embodiment of the invention, wherein at least one first pro-drug and at least one second pro-drug are administered contemporaneously.

In yet another embodiment of the invention, wherein at least one first pro-drug and at least one second pro-drug are administered in a sequential manner.

The invention claimed is:

1. A method for decapsulation of a pro-drug in vivo comprising steps of:
   a. administering an encapsulated pro-drug to a subject;
   b. locating a target site which has been dosed with said encapsulated pro-drug at a predetermined concentration; and
   c. exposing said target site to X-ray radiation of up to 250 keV;

wherein single exposure of said target site to said up to 250 keV X-ray radiation provides a maximal absorbed dose rate of at least 5 Gy/min at said target site, sufficient for decapsulation of said encapsulated pro-drug, whilst the maximal absorbed dose rate at an adjacent non target site within said subject is not more than 40% of said maximal dose rate at said target site.

2. The method according to claim 1, wherein said step of exposing said target site to X-ray radiation is characterized by providing a converging beam with increased average radiation flux cross section area density along longitudinal axis until reaching a maximum at said target site, said radiation is diverging with reduced radiation doses at tissues or cells preceding or following or surrounding said target site.

3. The method according to claim 1, wherein said X-ray radiation is characterized by photon energy in the range of between about 30 keV and about 180 keV.

4. The method according to claim 1, wherein said single exposure to said X-ray radiation of up to 250 keV provides at least one of the following:
   a. an absorbed dose rate of about 10 Gy/min at said target site;
   b. a maximal absorbed dose rate of at least 5 Gy/min at about 6 cm to about 8 cm depth under the skin surface of said subject; and
   c. a maximal absorbed dose rate at a focal depth of about 8 cm and focal spread diameter of about 5 mm.

5. The method according to claim 1, wherein said pro-drug is encapsulated by or attached to a delivery agent or vehicle, or wherein said pro-drug is encapsulated by or attached to delivery agent or vehicle comprising gold nanoparticles.

6. The method according to claim 1, comprising at least one additional step selected from the group consisting of:
   a. providing an in vivo reservoir of pro-drug and exposing said reservoir of pro-drug to X-ray in a predetermined manner to convert a predetermined quantity of said pro-drug to said active drug;
   b. exposing said target site to an X-ray administering protocol comprising a cell killing mode and a pro-drug-activating mode, said administering protocol modes are provided simultaneously, interchangeably or sequentially.

7. The method according to claim 1, comprising an additional step selected from the group consisting of:
   a. exposing said target site to X-ray doses in the range of between about 20 Gy to about 80 Gy, or to any other dosing protocol; and
   b. exposing said target site to X-ray doses in the range of between about 20 Gy to about 80 Gy, provided in 1.8 to 4 Gy fractions, or in any other dose fractioning protocol.

8. The method according to claim 1, comprising at least one additional step selected from the group consisting of:
   a. exposing said target site to a radiotherapy protocol or to a radiosurgery protocol or to a combination thereof;
   b. exposing said target site to X-ray radiation after or during or a combination thereof, administering said pro-drug; and
   c. designing said pro-drug so as to be activated after an enzymatic or chemical reaction.

9. The method according to claim 8, comprising an additional step of activating said enzymatic or chemical reaction by exposure to X-ray radiation; wherein said step of exposure to X-ray radiation is characterized by providing a converging X-ray of a controllable waist, substantially uniform at said target site, sufficient to convert said pro-drug to an active drug, whilst said X-ray photon dosage at said target site is higher than the X-ray photon dosage at an adjacent non target site.

10. The method according to claim 1, comprising at least one additional step selected from the group consisting of:
   a. selecting said pro-drug from the group consisting of oligonucleotides, antisense oligonucleotides, lipids, chemical molecules, chemical derivatives, biological molecules or derivatives thereof, precursors, analogs, antibodies, genes, enzymes, amino acids, proteins, metabolites, enantiomers, glycoproteins, lipoproteins, viral vectors, and any combination thereof;
   b. selecting said pro-drug from the group of types based on bioactivation site consisting of intracellular site, extracellular site, and a combination thereof;
   c. selecting said pro-drug from the group of types based on tissue location of bioactivation consisting of therapeutic target tissues or cells, metabolic tissues such as liver, gastrointestinal (GI) mucosal cell, lung, GI fluids, systemic circulation, extracellular fluid compartments, digestive fluids, blood, and any combination thereof; and
   d. selecting said pro-drug from the group consisting of nanoparticles, gold nanoparticles, high-Z nanomaterials, liposomes, encapsulating vehicle, pegylated liposomal formulation, immunoliposomes, peptide vectors, viral vectors, carrier mediated transporters, nanocarriers, nanospheres, nanocapsules, micelles, polymeric micelles, vesicles, polymers, drug conjugates, and any combination thereof.

11. The method according to claim 1, comprising at least one additional step selected from the group consisting of:
   a. providing said pro-drug with at least one carrier or delivery vehicle selected from the group consisting of implants, nanoparticles, encapsulating vehicle, high-Z nanomaterials, gold nanoparticles, liposomes, pegylated liposomal formulation, immunoliposomes, peptide vectors, viral vectors, carrier mediated transporters, nanocarriers, nanospheres, nanocapsules, micelles, polymeric micelles, vesicles, polymers, drug conjugates, and any combination thereof;
   b. encasing said pro-drug in a carrier or vehicle;
   c. tagging or attaching said pro-drug with an antibody or a ligand;
   d. encapsulating said drug or prodrug in an inactive configuration, further wherein said method comprises an additional step of activating said drug or pro-drug by decapsulation thereby providing the active drug;
   e. providing said pro-drug with at least one of: poly(butyl) cyanoacrylate (PBCA), Tween-80, apolipoprotein E, lipoprotein, and any combination thereof;
   f. The method according to claim 1, comprising an additional step of linking said pro-drug with peptide vectors or viral vectors; and
   g. The method according to claim 1, comprising an additional step of providing said pro-drug with substrates for transporters.

12. The method according to claim 11, comprising an additional step of tagging or attaching said carrier or vehicle with an antibody or a ligand.

13. The method according to claim 11, comprising an additional step of providing said pro-drug with substrates for transporters selected from the group consisting of influx transporters, efflux transporters, amino acid transporters, and any combination thereof.

14. The method according to claim 1, comprising at least one additional step selected from the group consisting of
   a. activating said pro-drug thereby targeting said active drug to a target tissue or cell or receptor;

b. enhancing drug delivery across the Blood Brain Barrier (BBB) prior, after, during or combinations thereof, administering said pro-drug or activating said pro-drug;

c. activating said pro-drug by a mechanism selected from the group consisting of oligomerization, polymerization, monomerization, cleavage, binding to a ligand, enzyme activation, chemical modification, radiolysis, excitation, formation of radicals, deprotonation, isomerization, reduction, oxidation, Enhanced Permeability and Retention (EPR) effect, and any combination thereof; and d. enhancing drug delivery across the BBB by at least one mechanism selected from the group consisting of: radiotherapy or X-ray irradiation, administering inhibitors of BBB transporters, disrupting the BBB, providing said pro-drug with substrates for influx transporters mediating endogenous substrate transport from the circulation into the parenchyma or central nervous system (CNS), and any combination thereof.

15. The method according to claim 14, comprising at least one additional step selected from the group consisting of
    a. selecting said BBB transporters from the group consisting of multidrug resistance (MDR) proteins, ATP-binding cassette (ABC) transporter proteins, P-glycoproteins (ABCB1), multidrug resistance protein-1 MRP-1 (ABCC1), multidrug resistance protein-2 MRP-2 (ABCC2), breast cancer resistance protein BCRP (ABCG2), and any combination thereof; and
    b. disrupting the BBB by at least one mechanism or agent selected from the group consisting of using hypertonic solutions such as mannitol, synthetic analogues such as receptor-mediated permeabilizer RMP-7, modulators, and any combination thereof.

16. The method according to claim 1, comprising at least one additional step selected from the group consisting of
    a. treating a disease, especially cancer, tumour or proliferative disease comprising benign, pre-malignant, or malignant neoplasm, brain and central nervous system (CNS) tumors, bladder cancer, breast cancer, cervical cancer, colorectal cancer, esophageal cancer, liver cancer, ovarian epithelial cancer, pancreatic cancer, pituitary tumour, prostate cancer, rectal cancer, kidney cancer, small intestine cancer, urine sarcoma, vaginal cancer;
    b. designing said encapsulated pro-drug so as to increase the bioavailability of antitumor drugs;
    c. designing said encapsulated pro-drug so as to increase the local delivery of antitumor drugs; and
    d. administering said pro-drug to said subject parenterally, intramuscularly, intradermally, topically, orally, intravenously, by injection, by infusion, by an implant, or by any combination thereof.

17. The method according to claim 1, wherein said photon dosage at said target site complies with the American College of Radiology (ACR), American Society of Radiologic Technologists (ASRT), American Society for Radiation Oncology (ASTRO) guidelines or any other treatment or safety guideline.

18. A protocol for decapsulating a pro-drug in vivo comprising the steps of:
    a. administering an encapsulated pro-drug to a subject;
    b. locating a target site which has been dosed with said encapsulated pro-drug at a predetermined concentration; and
    c. exposing said target site to X-ray radiation of up to 250 keV at predetermined doses and/or periodicities;

wherein a single exposure of said target site to said up to 250 keV X-ray radiation provides a maximal absorbed dose rate of at least 5 Gy/min at said target site, sufficient for decapsulation of said encapsulated pro-drug, whilst the maximal absorbed dose rate at an adjacent non target site within said subject is not more than 40% of said maximal dose rate at said target site.

19. A system for decapsulating a pro-drug in vivo comprising:
    a. An encapsulated pro-drug to be administered to a subject at a predetermined concentration; and
    b. X-ray emitting means for emitting an up to 250 keV photon energy beam to a target site within a subject which has been dosed with said encapsulated pro-drug at a predetermined concentration;

wherein said X-ray emitting means is characterized by the ability to provide, by a single exposure of said target site to said X-ray radiation of up to 250 keV, a maximal absorbed dose rate of at least 5 Gy/min at said target site, sufficient for decapsulation of said encapsulated pro-drug, whilst the maximal absorbed dose rate at an adjacent non target site within said subject is not more than 40% of said maximal dose rate at said target site.

20. The system according to claim 19, wherein at least one of the following holds true:
    a. said X-ray radiation is characterized by a converging beam with increased average radiation flux cross section area density along longitudinal axis until reaching a maximum at said target site, said radiation is diverging with reduced radiation doses at tissues or cells preceding or following or surrounding said target site;
    b. said pro-drug is encapsulated by or attached to a delivery agent or vehicle or wherein said delivery agent or vehicle comprises gold nanoparticles;
    c. said X-ray emitting means are configured for providing X-ray exposure to a target volume, said X-ray irradiating means comprising an X-ray beam and at least one focusing lens wherein said exposure is distributed over a volume of said target in a substantially uniform manner;
    d. said X-ray emitting means comprising:
        i. an X-ray emitting beam; and,
        ii. at least one focusing lens configured for focusing radiation emitted by said beam, said lens being axially symmetric; said lens comprising Bragg-type lens elements longitudinally arranged for Bragg X-ray diffraction of said radiation; wherein an emitting aperture of a variable shape of said beam is extendable such that said lens provides a substantially uniform converging X-ray beam of a controllable waist size comparable with dimensions of said target volume; and
    e. said system comprising at least one first pro-drug and at least one second pro-drug, wherein at least one of said pro-drugs is an encapsulated prodrug predesigned so as to be decapsulated upon a single exposure to a converging X-ray of up to 250 keV; said single exposure to said X-ray radiation of up to 250 keV provides a maximal absorbed dose rate of at least 5 Gy/min at said target site, sufficient for decapsulation of said encapsulated pro-drug, whilst the maximal absorbed dose rate at an adjacent non target site within said subject is not more than 40% of said maximal dose rate at said target site, said system of at least one first pro-drug and at least one second pro-drug, upon administration to a subject, provides a greater than additive therapeutic effect than if at least one of said pro-drugs was administered absent of said exposure to said converging X-ray.

\* \* \* \* \*